US00PP28062P2

(12) United States Plant Patent
Johnson, Jr.

(10) Patent No.: US PP28,062 P2
(45) Date of Patent: May 30, 2017

(54) ***HYDRANGEA* PLANT NAMED 'LITTLE ECHO'**

(50) Latin Name: *Hydrangea macrophylla*
Varietal Denomination: Little Echo

(71) Applicant: Ozzie W. Johnson, Jr., Marietta, GA (US)

(72) Inventor: Ozzie W. Johnson, Jr., Marietta, GA (US)

(73) Assignee: ITSAUL HORTICULTURE INC., Atlanta, GA (US)

( * ) Notice: Subject to any disclaimer, the term of this patent is extended or adjusted under 35 U.S.C. 154(b) by 132 days.

(21) Appl. No.: 14/545,897

(22) Filed: Jul. 1, 2015

(51) Int. Cl.
*A01H 5/00* (2006.01)

(52) U.S. Cl.
USPC ..... Plt./250

(58) Field of Classification Search
USPC ..... Plt./226, 250
See application file for complete search history.

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Hydrangea macrophylla* plant named, 'Little Echo', that is characterized by its well branched, compact plant habit, its flexible young stems that mature into strong stems that remain upright, its reblooming flowering habit, blooming on both old and new wood, its large mophead type inflorescences that are made up of a large number of individual sterile flowers, its inflorescences that are pastel pink to medium blue in color depending on soil pH, and its small seedpods that produce numerous, fine, dust-like seeds.

2 Drawing Sheets

Botanical classification: *Hydrangea macrophylla.*
Varietal denomination: 'Little Echo'.

BACKGROUND OF THE INVENTION

The present invention relates to a new and distinct cultivar of *Hydrangea macrophylla* and will be referred to hereafter by its cultivar name, 'Little Echo'. 'Little Echo' represents a new bigleaf *hydrangea*, a deciduous shrub grown for landscape use and for use as a potted plant in the lightly shaded landscape.

'Little Echo' was derived from an ongoing controlled breeding program conducted by the Inventor in Marietta, Ga. The objectives of the breeding program are to develop new cultivars of *Hydrangea* that exhibit reblooming flowering habits and unique foliage colors.

The Inventor made a cross in summer of 2010 between *Hydrangea macrophylla* 'Lemon Daddy' (U.S. Plant Pat. No. 17,660) as the female parent and *Hydrangea macrophylla* 'Shikizaki' (not patented) as the male parent. 'Little Echo' was selected as a single unique plant from the resulting seedlings in May of 2012.

Asexual propagation of the new cultivar was first accomplished by stem cuttings in Alpharetta, Ga. in September of 2011 by the Inventor. Asexual propagation by stem cuttings has determined that the characteristics of the new cultivar are stable and are reproduced true to type in successive generations.

SUMMARY OF THE INVENTION

The following traits have been repeatedly observed represent the characteristics of the new cultivar. These attributes in combination distinguish 'Little Echo' as a unique cultivar of *Hydrangea macrophylla.*

1. 'Little Echo' exhibits a well-branched, compact plant habit.
2. 'Little Echo' exhibits flexible young stems arching under the weight of inflorescences that mature into strong stems that remain upright.
3. 'Little Echo' exhibits a reblooming flowering habit, blooming on both old and new wood.
4. 'Little Echo' exhibits large mophead type inflorescences that are made up of a larger number of individual sterile flowers when compared to other mophead type *Hydrangea* cultivars.
5. 'Little Echo' exhibits inflorescences that are pastel pink to medium blue in color depending on soil pH and aluminum concentration.
6. 'Little Echo' exhibits small seedpods that produce numerous, fine, dust-like seeds.

The female parent of 'Little Echo, 'Lemon Daddy' differs from 'Little Echo' in having foliage that is yellow in color, in having stems and leaves that are thicker in substance, in having fewer sterile flowers that are larger in size, and in having a single blooming habit that only blooms on old wood. The male parent of 'Little Echo', 'Shikizaki', is similar to 'Little Echo' in having a reblooming flowering habit. 'Shikizaki' differs from 'Little Echo' in having inflorescences that are darker in color, in having foliage that is larger in size, and in being more sensitive to changes in pH and aluminum concentration. 'Little Echo' can be most closely compared to the *Hydrangea macrophylla* cultivars 'Bailmer' (U.S. Plant Pat. No. 15,298) and 'Wyatt LeFever' (not patented). 'Bailmer' is similar to 'Little Echo' in having similarly sized inflorescences and in having a reblooming mophead plant habit. 'Bailmer' differs from 'Little Echo' in having foliage that is larger in size, in having flower color that is more sensitive to changes in pH and aluminum concentration, in have fewer sterile flowers that are larger in size, in having more fertile flowers, and in having a weaker tendency to rebloom. 'Wyatt LeFever' is similar to 'Little Echo' in having a reblooming mophead plant habit. 'Wyatt LeFever' differs from 'Little Echo' in having foliage that is larger in size, in having flower color that is more sensitive to changes in pH and aluminum concentration, in have fewer sterile flowers that are larger in size, in having a weaker tendency to rebloom, and in having inflorescences that are smaller, rounder, and darker in color.

BRIEF DESCRIPTION OF THE DRAWINGS

The accompanying colored photographs illustrate the overall appearance and distinct characteristics of the new *Hydrangea.*

The photographs of FIG. 1 and FIG. 3 were taken of three year-old plants of 'Little Echo' as grown in a greenhouse in five-gallon containers in Atlanta, Ga.

Figure 3:
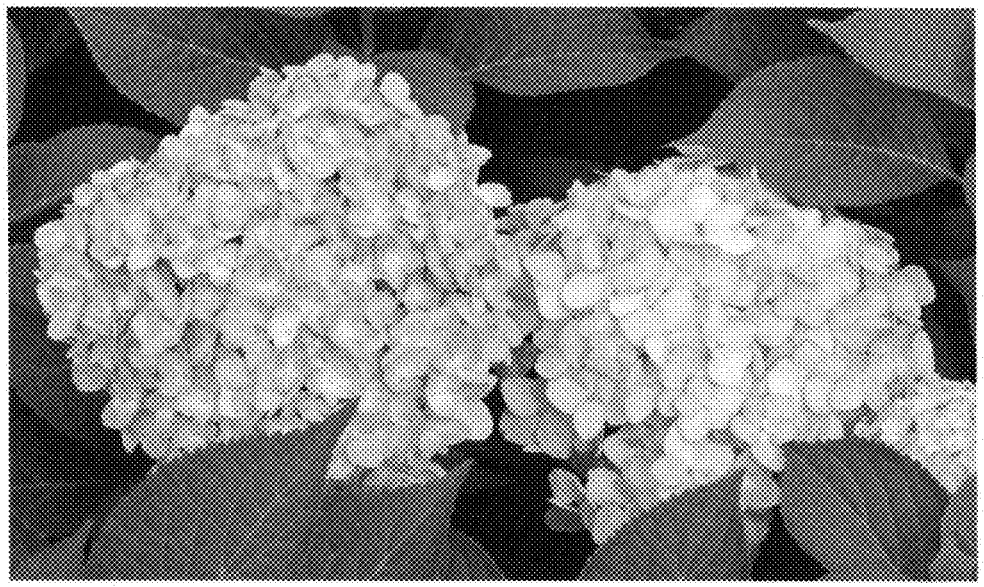

The photograph in FIG. 3 was taken of a three year-old plant of 'Little Echo' as grown outdoors in acidic soil, in Gainesville, Ga.

Figure 1:
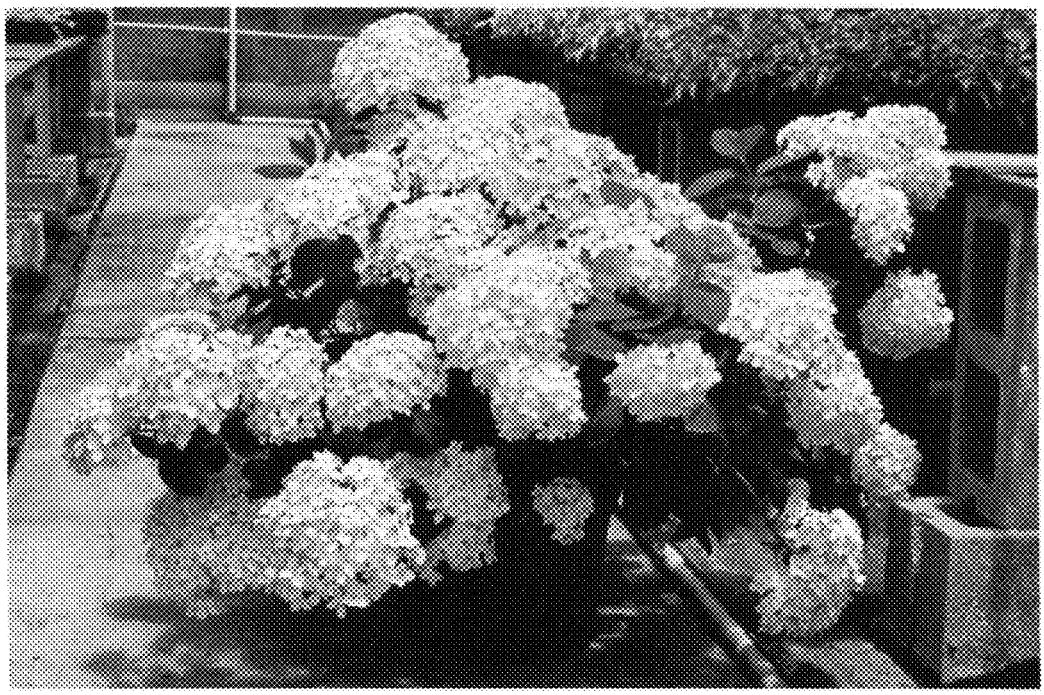

The photograph in FIG. 1 provides a side view of the flowering habit of a plant of 'Little Echo' as grown in alkaline soil.

Figure 2:
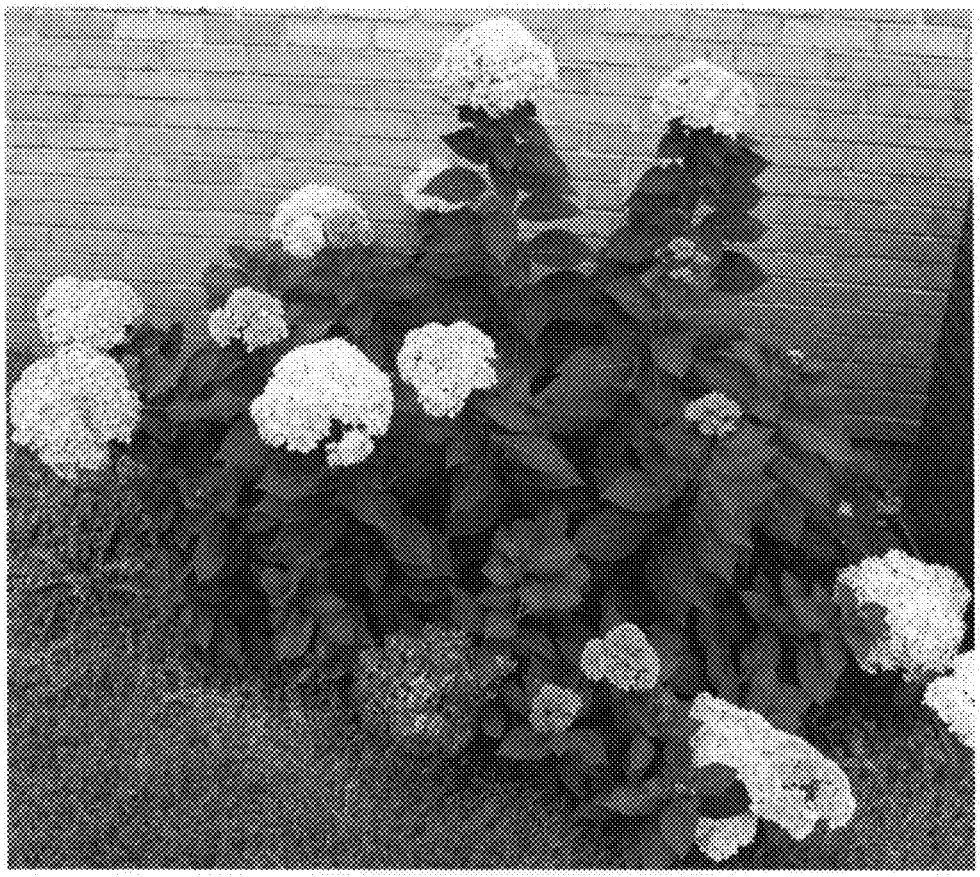

The photograph in FIG. 2 provides a top view of a plant of 'Little Echo' in bloom as grown in acidic soil, with aged bloom at bottom.

The photograph in FIG. 3 provides a close-up comparison view of inflorescences of 'Little Echo' as grown on acidic soil (left) and alkaline soil (right).

The colors in the photographs are as close as possible with the digital photography and printing techniques utilized and the color codes in the detailed botanical description accurately describe the new *Hydrangea.*

BOTANICAL DESCRIPTION OF THE PLANT

The following is a detailed description of three year-old plants of the new cultivar as grown in five-gallon containers under greenhouse conditions in Atlanta, Ga. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period.*—Beginning in late spring (late May to early June) and continuing to set buds and open flowers with colorful blooms until hard frost, in Georgia.

*Plant type.*—Deciduous shrub, bigleaf *hydrangea*, Hortensia type.

*Plant habit.*—Upright, open mound, compact.

*Height and spread.*—An average of 1.2 m in height and 1.4 m in width after three years of growth.

*Cold hardiness.*—At least to U.S.D.A. Zone 5b.

*Diseases and pests.*—Moderate resistance to leaf spot (*Cercospora hydrangeae*) has been observed, no susceptibility to insect problems has been observed.

*Root description.*—Fine.

*Propagation.*—Softwood stem cuttings.

*Growth rate and vigor.*—Vigorous with new shoot production.

*Root development.*—Roots initiate in 14-21 days and fully develop in a 5×7 cm container in six weeks.

Stem description:

*Stem shape.*—Round, solid.

*Stem strength.*—Strong.

*Stem color.*—New growth; 144D with lenticels 183A, mature wood; a blend of 165A and 199D.

*Stem size.*—An average of 40 cm in length (to inflorescence base) and 5 mm in width.

*Stem surface.*—New growth; glabrous, dull, densely covered with lenticels; about 32 per cm, about 3 mm in length and <0.5 mm in width, mature; smooth bark can split and peel.

*Branching.*—Basal branching with over 35 branches per plant, sublateral branching determined by pinching; 2 stems develop per pinched node.

Foliage description:

*Leaf shape.*—Elliptic.

*Leaf arrangement.*—Opposite.

*Leaf division.*—Simple.

*Leaf number.*—An average of 14 (7 pairs) per lateral branch 40 cm in length.

*Leaf base.*—Cuneate.

*Leaf apex.*—Acuminate to slightly caudate.

*Leaf margins.*—Serrated, an average of 18 per side on a leaf 8 cm in length.

*Leaf venation.*—Pinnate, recessed on upper surface and raised on lower surface, color 145B on upper surface and 145D on lower surface.

*Leaf size.*—An average of 10 cm in length and 5 cm in width when mature.

*Leaf attachment.*—Petiolate.

*Internode length.*—An average of 5 cm.

*Leaf surface.*—Glabrous and dull, finely puberulent on veins.

*Leaf color.*—Upper surface; 138A, lower surface; color 138B to 138C, leaf buds; 138C.

*Petioles.*—An average of 2.5 cm in length and 2.5 mm in width, color; 144C flushed with 181D towards base, glabrous surface.

Inflorescence description:

*Inflorescence type.*—Terminal compound globose corymb primarily comprised of rotate shaped sterile flowers with few fertile flowers.

*Lastingness of inflorescence.*—Persistent, but fresh color is retained for about 3 to 4 weeks.

*Inflorescence number.*—One per lateral or sublateral stem if pinched.

*Inflorescence size.*—An average of 11 cm in depth and 20 cm in diameter.

*Flower number.*—An average of 300 sterile flowers and 2 fertile flowers per corymb.

*Flower fragrance.*—None.

*Flower aspect.*—Upright at stem terminus.

*Flower size.*—Sterile flowers; an average of 2 cm in diameter and 3 mm in depth, fertile flowers; an average of 4 mm in diameter and 1.5 mm in depth.

*Flower buds.*—Sterile flowers; an average of 4 mm in length and 3 mm in diameter prior to opening, globose to ovate in shape, 157C in color prior to opening, fertile flowers; an average of 1 mm in length and 2.5 mm in diameter, orbicular in shape, 144B in color.

*Peduncles.*—For each complex corymb in inflorescence; an average of 8 mm in length and 1 mm in width, 149D in color, glabrous surface, secondary and tertiary corymbs; an average of 1.5 cm in length and 1 mm in width, 149D in color, glabrous surface, peduncle leaves; an average of 3 per inflorescence, up to 2 cm in length and 1.5 cm in width, elliptic in shape, same coloration and surface as stem leaves.

*Pedicels.*—Sterile flowers; an average of 3 cm in length and 1 mm in width, held at an average angle of 20° to 45° to vertical, 157D in color, fertile flowers; an average of 8 mm in length and <1 mm in width, NN155A in color, glabrous surface on all flowers.

*Petals.*—(Grown under acidic conditions): sterile flowers; curled into eye zone (occasionally open when reproduction organs are present), N88A in color, an average of 1 mm in diameter and depth, fertile (flowers; 5, rotate in arrangement, oval to elliptic in shape, entire margin, acute apex, cuneate base, an average of 1.5 mm in length and 2 mm in width, upper and lower surface is glabrous and dull, color; of upper and lower surface a blend of N88A to N88C and 95B to 95D.

*Sepals.*—Sterile flowers; an average of 4, rotate in arrangement, broadly ovate in shape, entire margin, broadly acute apex, cuneate base, an average of 7 mm in length and 6 mm in width, upper and lower surfaces are glabrous and dull, color; upper and lower surfaces when opening under all conditions 144D, upper and lower surfaces when fully open and grown under acidic conditions; a blend of 91B to 91D, 97A to 97B and 100C to 100D, upper and lower surfaces when fully open and grown under alkaline conditions; 75B to 75D, with sun exposure color fades to a mix of 143D and 178B on the upper surface and a mix of 178B and 182D on the lower surface, fertile flowers; 5, ovate in shape, entire margins, acute apex, cuneate base, an average of 0.75 mm in length and 0.5 mm in width, upper and lower surfaces glabrous and smooth, color 144B.

Reproductive organs: (Fertile flowers and occasionally present in sterile flowers, grown under acidic conditions).

*Stamens.*—An average of 3, anthers; deltoid in shape, basifixed, minute in size, and 99B to 99C in color, filament; an average of 1 mm in length and 99D in color, pollen is low in abundance and 162D in color.

*Pistils.*—1, stigma is minute in size and 99B in color, style is an average of 1 mm in length and 99D in color, ovary is minute in size and 99D in color.

Fruit and seed: Seed pods are <2 mm in height and 1 mm in diameter, numerous dust-like seeds (too small to determine a color reading).

It is claimed:

1. A new and distinct cultivar of *Hydrangea* plant named 'Little Echo' substantially as herein illustrated and described.

* * * * *